(12) United States Patent
Scommegna et al.

(10) Patent No.: US 8,246,349 B2
(45) Date of Patent: Aug. 21, 2012

(54) ORTHODONTIC BRACKET

(75) Inventors: Gabriele Scommegna, Tavarnuzze Impruneta (IT); Maurizio Dolfi, Florence (IT)

(73) Assignee: Leone S.p.A., Sesto Fiorentino (FI) (IT)

( * ) Notice: Subject to any disclaimer, the term of this patent is extended or adjusted under 35 U.S.C. 154(b) by 231 days.

(21) Appl. No.: 12/531,928

(22) PCT Filed: Jul. 23, 2007

(86) PCT No.: PCT/IT2007/000517
§ 371 (c)(1),
(2), (4) Date: Sep. 18, 2009

(87) PCT Pub. No.: WO2008/114297
PCT Pub. Date: Sep. 25, 2008

(65) Prior Publication Data
US 2010/0105000 A1    Apr. 29, 2010

(30) Foreign Application Priority Data

Mar. 22, 2007    (IT) .................................. FI2007A0069

(51) Int. Cl.
*A61C 3/00*    (2006.01)
(52) U.S. Cl. ........................................... 433/13; 433/10
(58) Field of Classification Search ................ 433/8–18, 433/22
See application file for complete search history.

(56) References Cited

U.S. PATENT DOCUMENTS

| | | | |
|---|---|---|---|
| 2,549,528 A | 4/1951 | Russell | |
| 5,322,435 A | 6/1994 | Pletcher | |
| 5,326,259 A | 7/1994 | Rohlcke et al. | |
| 5,622,494 A | 4/1997 | Andreiko et al. | |
| 5,711,666 A | 1/1998 | Hanson | |
| 6,485,299 B1 | 11/2002 | Wildman | |
| 7,731,496 B2 * | 6/2010 | Minium | 433/24 |
| 2002/0110772 A1 | 8/2002 | Abels et al. | |
| 2004/0166459 A1 | 8/2004 | Voudouris | |

(Continued)

FOREIGN PATENT DOCUMENTS

EP    0 876 801 A1    11/1998

(Continued)

*Primary Examiner* — Cris L Rodriguez
*Assistant Examiner* — Edward Moran
(74) *Attorney, Agent, or Firm* — McGlew and Tuttle, P.C.

(57) ABSTRACT

An orthodontic bracket including a body (1) having a mesio-distal slot (10), a base (11), and a plurality of tie wings (12, 120) mainly developed along an occlusal-gingival direction. The tie wings are provided two-by-two on opposite sides in relation to the slot (10) and partially emerging over a labial side (L) of the body (1). The slot (10) is apt to receive an archwire (2). The tie wings (12, 120) protrude externally from the body (1) and towards the base (11), feature a curved surface (121) whose concavity is turned towards the same base (1) and constitute a support for an element (3) apt to prevent the archwire (2) from coming out of the slot (10). The element (3) features a planar portion intended to slide above, and parallel to, the labial side (L) of the body (1) and a flexible and elastic arm (33) having a portion (34) which is securable to the surface (121) of two tie wings (12) resulting on the same side in relation to the slot (10). The portion (34) of the flexible arm (33) moves along a curved path corresponding to the profile of the lower side (LT) of the tie wings (12) while the planar portion of the element (3) slides above the labial side (L) of the bracket body (1).

19 Claims, 12 Drawing Sheets

U.S. PATENT DOCUMENTS

| | | |
|---|---|---|
| 2005/0239012 A1 | 10/2005 | Bathen et al. |
| 2005/0244775 A1 | 11/2005 | Abels et al. |
| 2005/0266368 A1 | 12/2005 | Abels et al. |
| 2006/0051721 A1 | 3/2006 | Carrier Lluch |
| 2006/0177790 A1 | 8/2006 | Farzin-Nia et al. |
| 2006/0228664 A1 | 10/2006 | Castner et al. |
| 2007/0248928 A1 * | 10/2007 | Damon ............ 433/10 |

FOREIGN PATENT DOCUMENTS

| | | |
|---|---|---|
| EP | 1 287 789 A2 | 3/2003 |
| WO | WO 2007/038737 | 4/2007 |

* cited by examiner

ORTHODONTIC BRACKET

The present invention relates to an orthodontic bracket.

In particular, the present invention relates to an orthodontic bracket of the "self-ligating" type.

It is known that, in orthodontics, use of orthodontic brackets cemented to the teeth of a dental arch is widely diffused. Such brackets, comprise a transverse slot crossed by a suitably shaped metallic archwire which, due to its elasticity properties, transmits to the teeth a set of forces which determine their movement according to a predetermined scheme, to obtain a more correct functional, biological and aesthetical positioning of the teeth. Examples of orthodontic brackets are described in EP 876801, U.S. Pat. No. 5,622,494 and U.S. Pat. No. 5,326,259.

To prevent the archwire coming out of the bracket's slots, i.e. to hold the archwire within the slots of the brackets, a ligating device, commonly called "ligature", is applied to each bracket. In its simplest form, such a ligating device is an elastic ring.

Referring to "self-ligating" brackets, the ligating device is generally constituted by a mobile element which is connected to the bracket's body so that it can assume a slot opening position, to allow positioning of the archwire inside the slot, and a slot closing position, so that the slot is closed by the mobile element and the archwire cannot come out of the slot.

Generally speaking, such a mobile element is connected to the bracket's body so that it can rotate in relation to the latter, the opening and closing of the slot being obtained by rotating the mobile element, or it can be connected to the bracket's body so that it can slide over the labial side of the bracket, the opening and closing of the slot being obtained by moving the mobile element along an occlusal-gingival direction.

Examples of "self-ligating" orthodontic brackets wherein the aforementioned mobile element can rotate in relation to the bracket's body are disclosed in US20050266368, US20050244775, US20020110772 and U.S. Pat. No. 6,485,299.

Examples of "self-ligating" orthodontic brackets in which the element which opens or closes the slot can slide over the bracket's labial side are described in U.S. Pat. No. 5,322,435, US20050239012, US20060051721, U.S. Pat. No. 2,549,528 and US20060177790.

U.S. Pat. No. 5,711,666 discloses an orthodontic bracket comprising a bracket body with a mesial distal extending arch wire slot and a ligating latch spring member having the form of a thin flat metal strip. The spring member comprises, along its length, an anchor portion anchored in the bracket body, a flexing portion in which the majority of the flexing takes place, a ligating portion that closes the slot mouth and engages any arch wire therein, and a latching portion by which the spring member is latched to the bracket body. The spring member comprises a biasing portion between the flexing and ligating portions at the slot occlusal surface, or between the ligating and latching portions at the slot gingival surface, this biasing portion being convex toward the slot lingual wall and protruding into the slot to press the arch wire into the respective slot wall junction for more precise control. The bracket body is made as two mirror image parts which are laser welded together and between which the spring member is mounted. The latches between the spring member and the bracket body comprise notches in the spring edges that are engaged by latch sears on the body, and two labially lingually spaced sears are provided. The spring member is made of a nickel titanium shape memory alloy. The bracket body has two pairs of tie wings for reception of an external ligature between which the spring member is disposed.

Drawbacks derive from the "self-ligating" orthodontic brackets commonly available on the market, both for the cumbersome presence of the mobile element, and for the high production costs which are due to the very complex realization and assemblage of the single parts. Further drawbacks derive from the difficult use of such known brackets during orthodontic therapy.

The present invention relates to an orthodontic bracket of the type comprising a slot opening/closing mobile element which can slide over the labial side of the bracket and it aims at simplifying the production of this type of bracket and, at the same time, at reducing its cost and size, increasing its reliability and safety and simplifying its use.

This result has been achieved, according to the invention, by adopting the idea of making an orthodontic bracket having the characteristics disclosed in claim 1. Further characteristics of the present invention are dealt with in the dependent claims.

Thanks to the present invention, it is possible to realize a "self-ligating" orthodontic bracket which, with respect to the known self-ligating orthodontic brackets, is cheaper, more compact, more reliable, more versatile, safer and easier to make.

To further clarify the above and other advantages and features of the present invention, a more particular description of the invention will be rendered by reference to specific embodiments thereof which are illustrated in the appended drawings. It is appreciated that these drawings depict only typical embodiments of the invention and are therefore not to be considered limiting of its scope. In the appended drawings.

Figure 1:
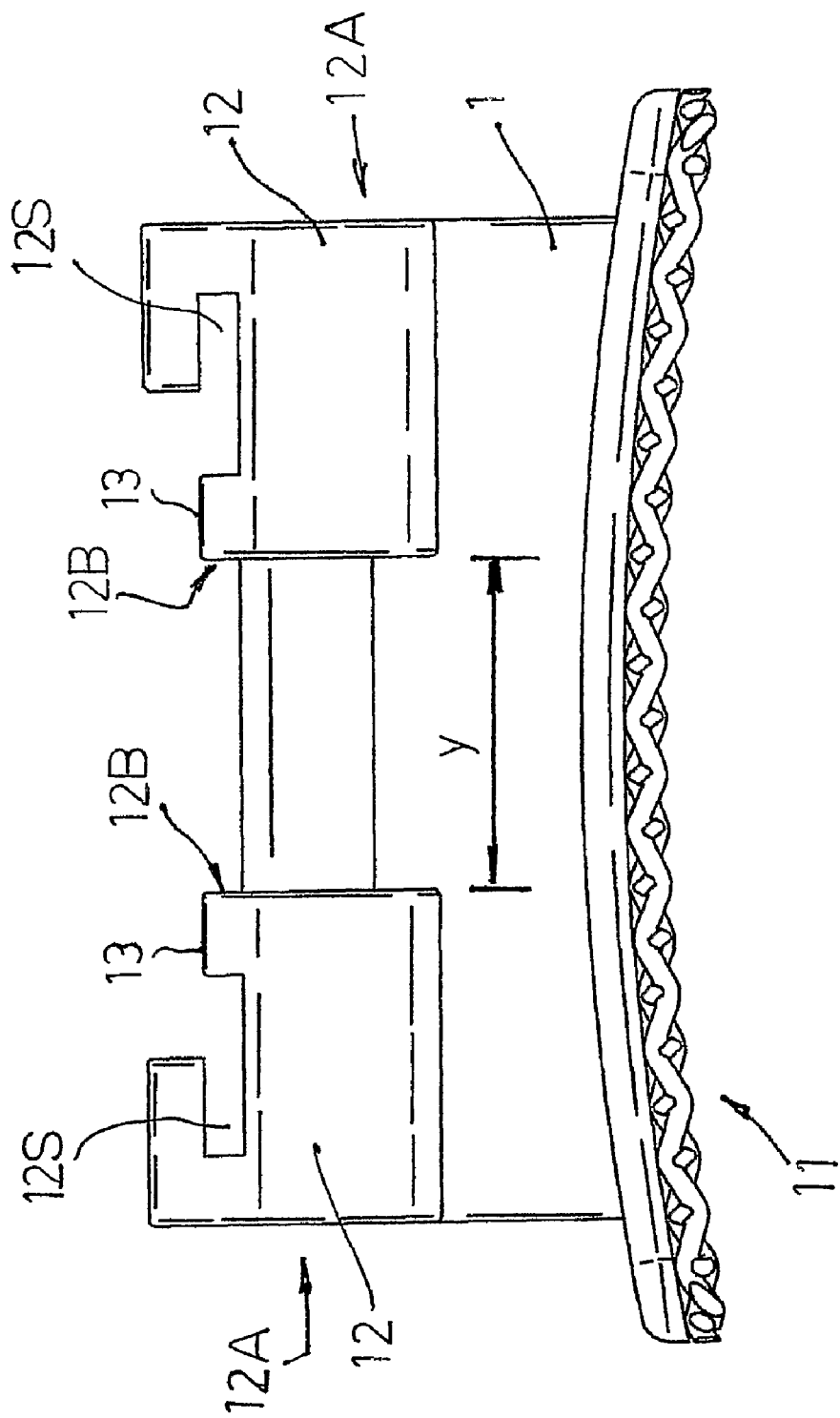
FIG. 1 shows a rear view of the body of an orthodontic bracket according to the present invention.
Figure 2:
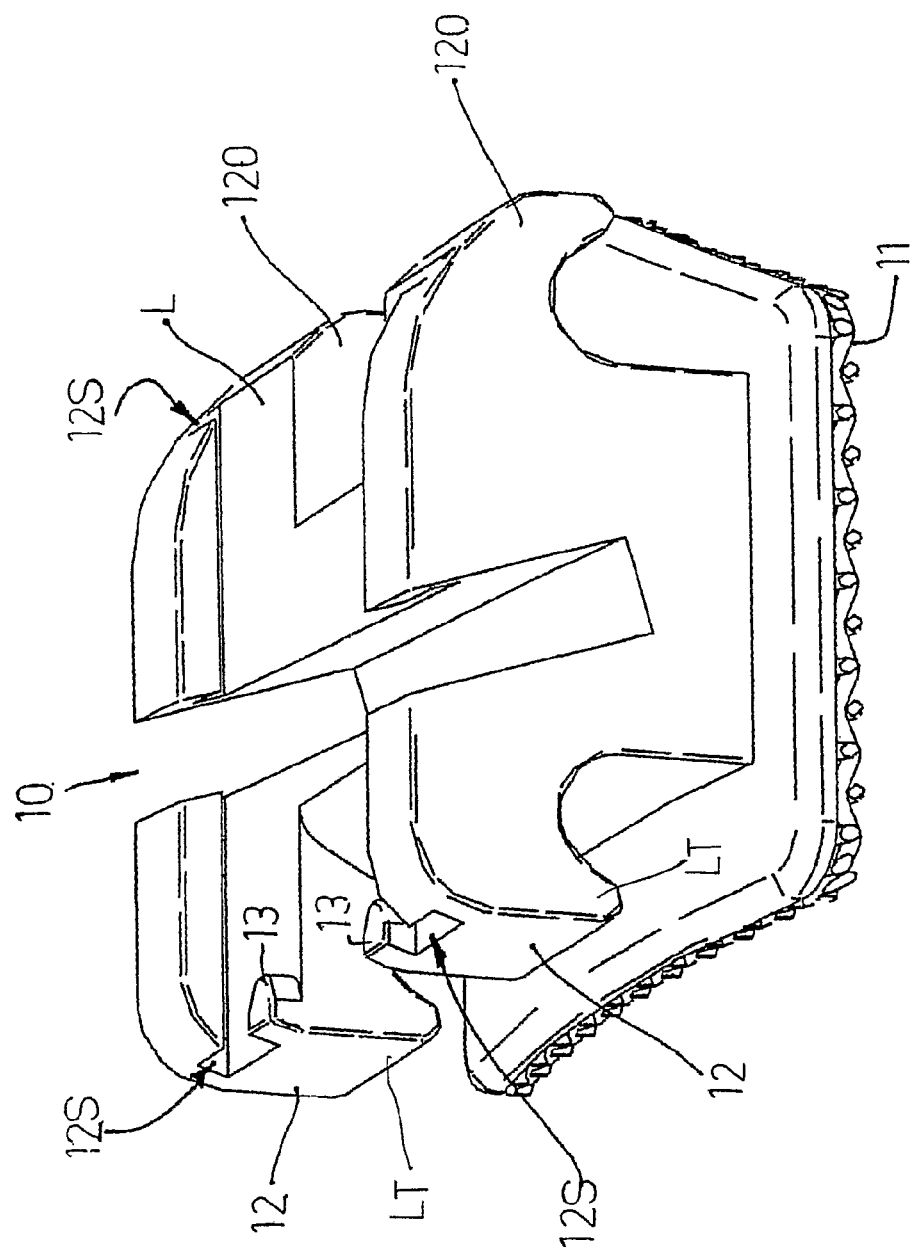
FIG. 2 is a perspective view of the bracket's body shown in FIG. 1.

Reduced to its basic structure and reference being made to the appended drawings, an orthodontic bracket according to the present invention comprises a body (1) having a slot (10) along a mesiodistal direction, a base (11) through which the bracket is bonded to a tooth (D) of the dental arch to be treated (for example, bonded to the vestibular side of the crown), and a plurality of tie wings (12, 120) which extend along an occlusal-gingival direction on opposite sides of the slot (10) and are partially emerging above the labial side (L) of the body (1). Inside the slot (10), an archwire (2) can be positioned. For example, the archwire (2) can be made of a shape-memory type Ni—Ti alloy and it can have a circular cross section. The tie wings (12, 120) project externally from the bracket and towards the base (11), feature a curved surface (121)—which in jargon is called "underwing"—whose concavity is turned towards the base (11), and constitute supporting parts for an element apt to hold the archwire (2) inside the slot (10).

The base (11) is bonded to the desired tooth by means of an orthodontic adhesive or cement.

The step of bonding the bracket to the tooth, as well as the structure, the positioning and the function of the archwire (2), i.e. the interaction between the archwire, the bracket and the tooth, are known to everyone skilled in the art and, therefore, they are not described in further details.

The present bracket comprises an element (3) connected to the body (1) so that it can slide along an occlusal-gingival direction above the labial side of the same body. Said element is destined to obtain covering and, respectively, opening of the underlying slot (10).

In other words, said element (3) is utilized to open or close the slot (10), that is, to allow access to the slot or to hold the archwire (2) inside it.

According to the example shown in the appended drawings, said tie wings (12, 120) are four in number and are positioned, two-by-two, on opposite sides with respect to the slot (10), i.e. they form a pair of occlusal tie wings (12) and a pair of gingival tie wings (120).

Furthermore, said tie wings (12, 120) have an external occlusal-gingival side (12A) and an inner occlusal-gingival side (12B) and they feature a groove (12S) which, as further described below, acts as a guide for the element (3).

Reference being made to the example shown in the appended drawings, all said grooves (12S) are on the labial side of the body (1), are rectilinear and each of them has the same length of the respective tie wing.

Furthermore, since said tie wings (12, 120) are two-by-two on opposite sides of the slot (10), each of the said grooves (12S) is aligned with a corresponding groove (12S) resulting on the opposite side in relation to the slot (10).

Said body (1) is provided with an appendix (13) orthogonally emerging from its labial side (L), on the inner side (12B) of each of said occlusal tie wings (12).

The said appendixes (13) act, as further described below, as a means for stopping the element (3) when the latter is moved to open the slot (10).

The said element (3) is made of a thin plate, for example of stainless steel, having an anterior edge (30), a rear zone (31), and two sides (32) destined to slide within the guides constituted by the said grooves (12S).

The said element (3) has an elastically flexible arm (33) centrally positioned between the said sides (32) so as to protrude with respect to the rear ends (320) of the sides (32), and is provided with a rear appendix (34) which is orthogonally oriented with respect to the same arm, i.e. it is mainly developed along a mesio-distal direction. In other words, when seen in plan view, the said element (3) is "E"-shaped, with an elastically flexible central portion (33) protruding beyond the others (32) and provided with a transverse appendix (34) on its free end. Yet in other words, the said element (3) has, on the side opposite to its anterior edge (30), i.e. on its rear portion, a flexible and elastic part (33) which is mainly developed along an occlusal-gingival direction, protrudes beyond the ends (320) of its sides (32) and has a transverse appendix (34). In practice, the central arm (33) of the "E"-shaped element (3) is longer than the others (32).

The said sides (32) of the element (3) are united to the central arm (33)—on the end (330) of the arm (33) which is opposite the end provided with the transverse appendix (34)—by the same material which the element (3) is made of. In practice, the longitudinal edges (331) of the central arm (33) are spaced from the inner edges (321) of the said sides (32), so that the central arm (33) can flex; furthermore, at the two sides of the said end (330) of the arm (33) there are two corresponding concave surfaces (35), whose height is equal to the thickness of the element (3), and whose concavity is turned towards the rear part of the element (3), i.e. is turned towards the appendix (34) of the arm (33).

As further described below, when the slot (10) is open, i.e. when the element (3) is moved backwards, each of the said surfaces (35) is intercepted by a respective appendix (13) of the body (1).

The length (x) of the aforementioned appendix (34) is greater than the distance (y) between the inner sides (12B) of two tie wings (12) resulting on the same side in relation to the slot (10). For example, the said length (x) is 15÷40% greater than the said distance (y) (x=1.15÷1.40 y). Preferably, the said length (x) is less than the distance between the external sides (12A) of two tie wings (12) resulting on the same side in relation to the slot (10).

Figure 3:
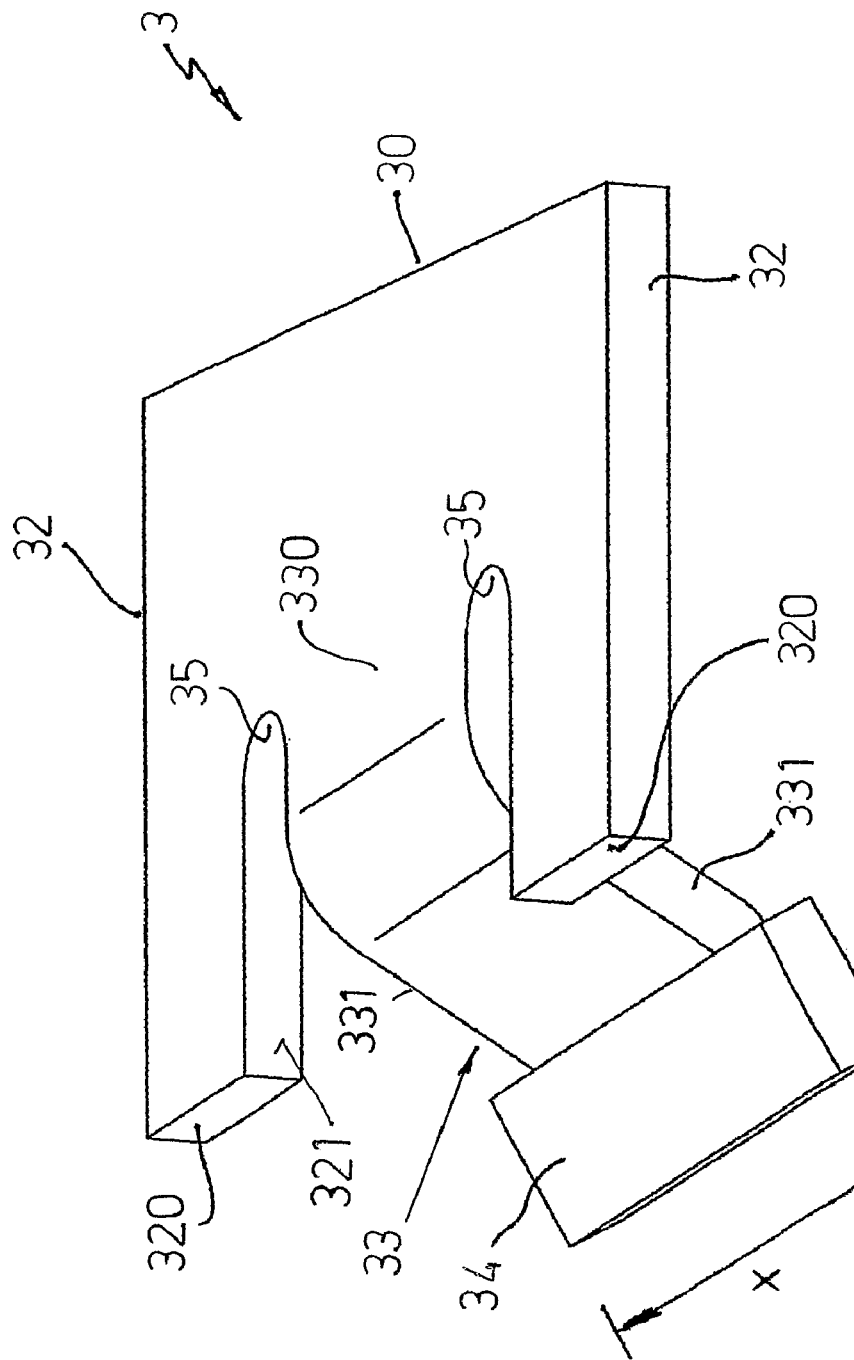
FIG. 3 is a perspective view of the element destined to open/close the slot featured by the body of the bracket shown in FIGS. 1 and 2.
Figure 4:
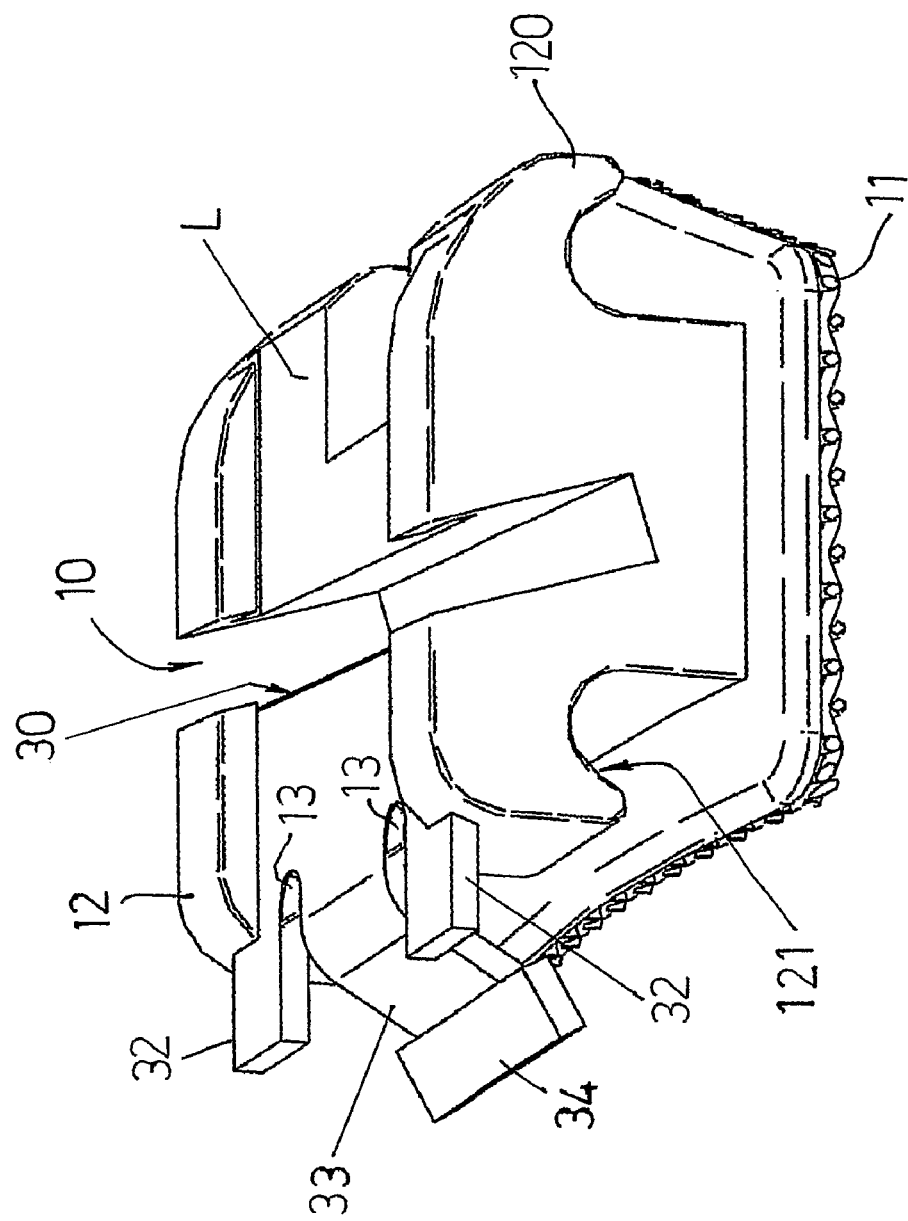
FIG. 4 shows an orthodontic bracket according to the present invention, the slot being open or accessible.
Figure 5:
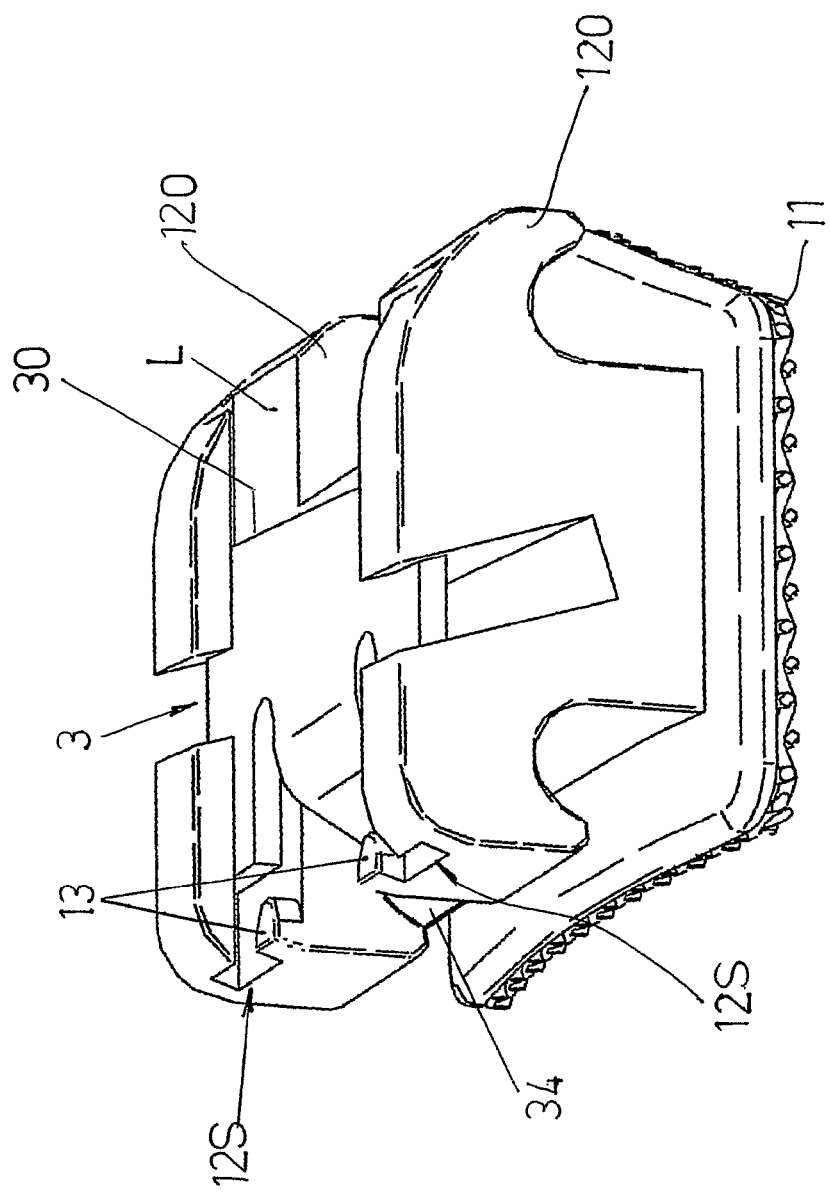
FIG. 5 shows the same orthodontic bracket of FIG. 4 but the slot is closed.
Figure 6A:
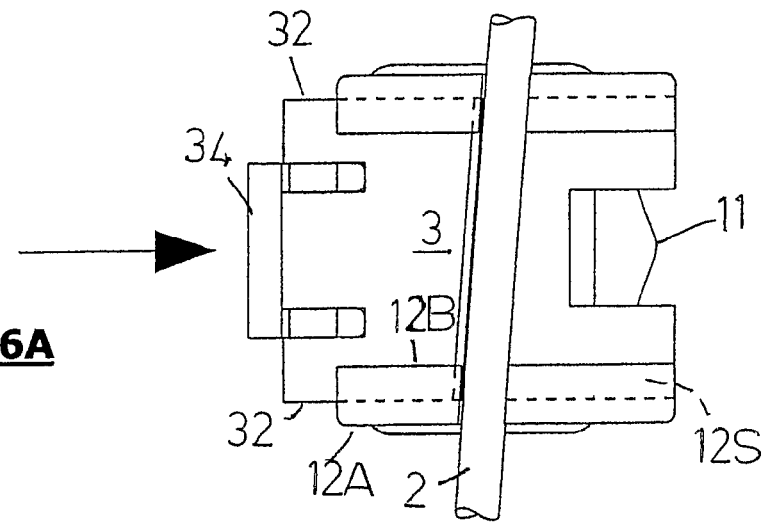
FIG. 6A is a plan view relating to one position of the mobile element as the mobile element moves from the open to the closed slot position.
Figure 6B:
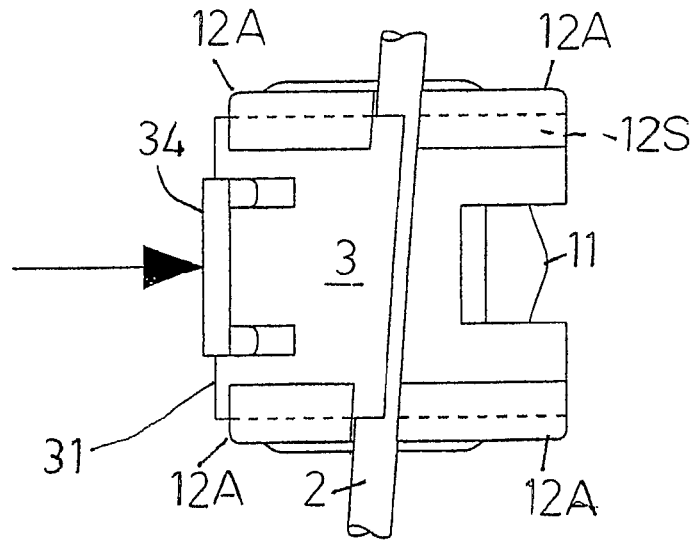
FIG. 6B is a plan view relating to another position of the mobile element as the mobile element moves from the open to the closed slot position.
Figure 6C:
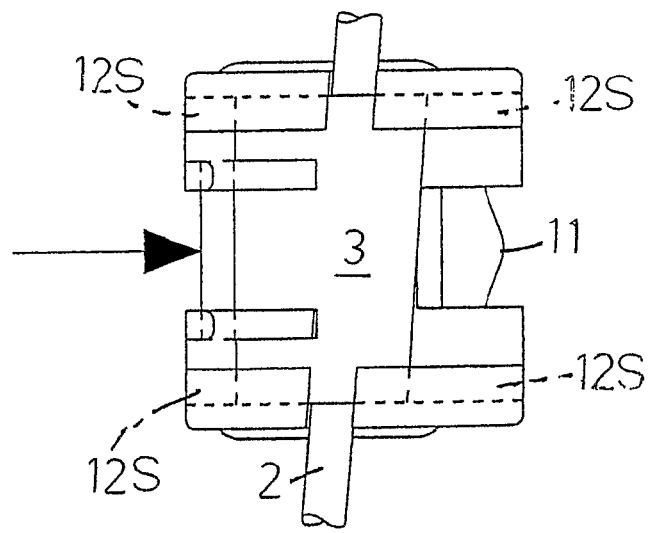
FIG. 6C is a plan view relating to yet another position of the mobile element as the mobile element moves from the open to the closed slot position.
Figure 7A:
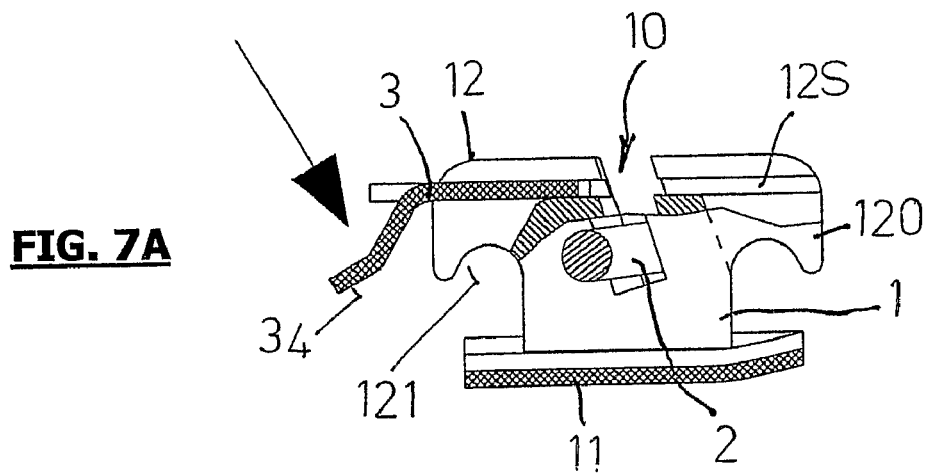
FIG. 7A is a side view, with partially sectioned parts, relating to one position of the mobile element as the mobile element moves from the open to the closed slot position as in FIG. 6A.
Figure 7B:
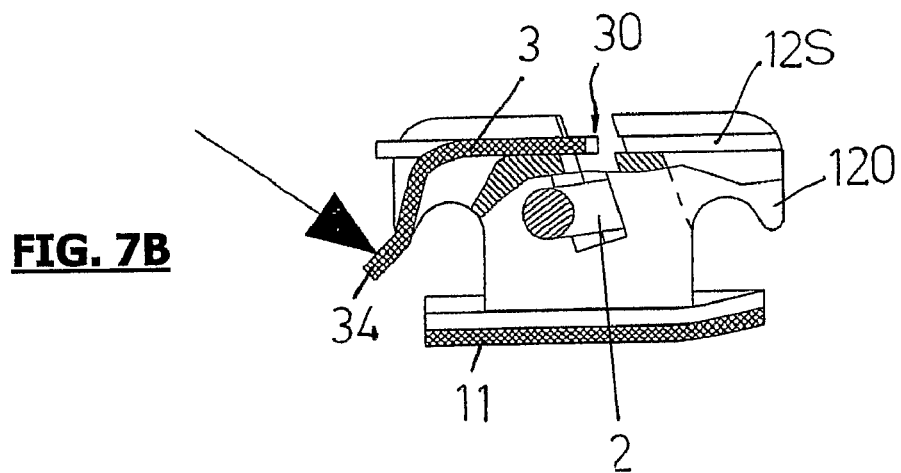
FIG. 7B is a side view, with partially sectioned parts, relating to another position of the mobile element as the mobile element moves from the open to the closed slot position as in FIG. 6B.
Figure 7C:
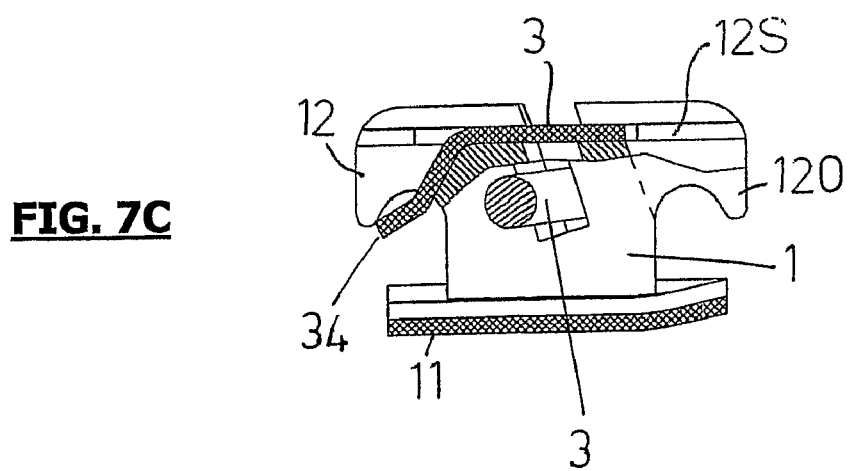
FIG. 7C is a side view, with partially sectioned parts, relating to yet another position of the mobile element as the mobile element moves from the open to the closed slot position as in FIG. 6C.
Figure 8A:
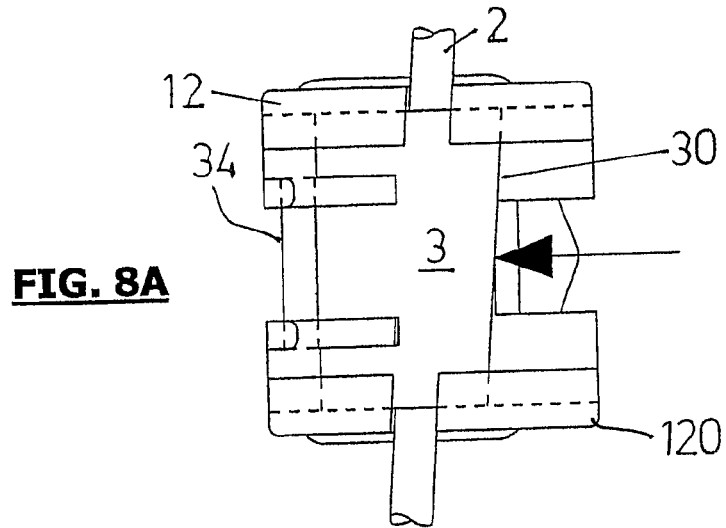
FIG. 8A is a plan view relating to one position of the mobile element as the mobile element moves from the closed to the open slot position.
Figure 8B:
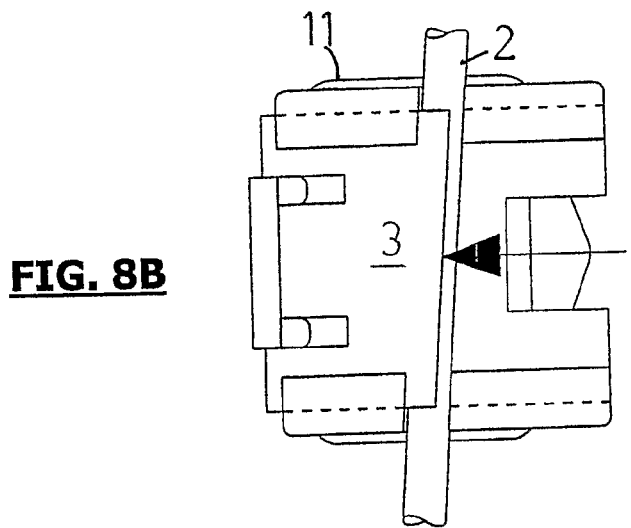
FIG. 8B is a plan view relating to another position of the mobile element as the mobile element moves from the closed to the open slot position.
Figure 8C:
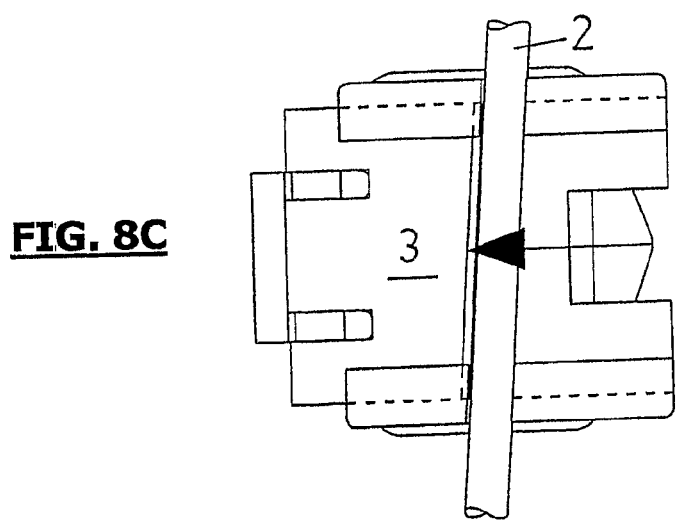
FIG. 8C is a plan view relating to yet another position of the mobile element as the mobile element moves from the closed to the open slot position.
Figure 9A:
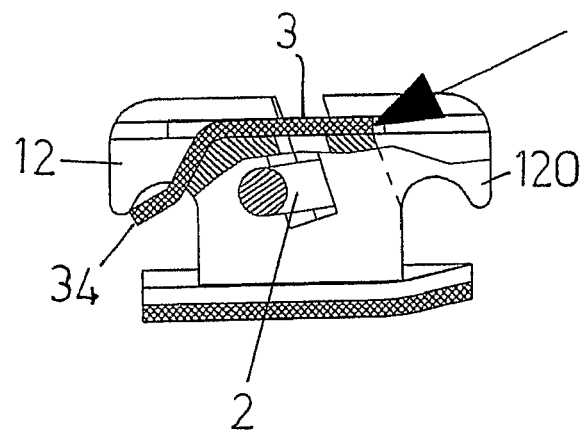
FIG. 9A is a side view, with partially sectioned parts, relating to one position of the mobile element as the mobile element moves from the open to the closed slot position as in FIG. 8A.
Figure 9B:
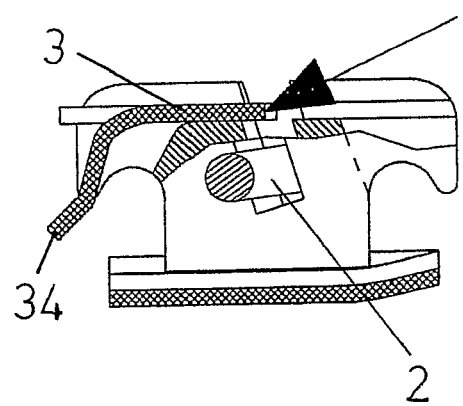
FIG. 9B is a side view, with partially sectioned parts, relating to another position of the mobile element as the mobile element moves from the open to the closed slot position as in FIG. 8B.
Figure 9C:
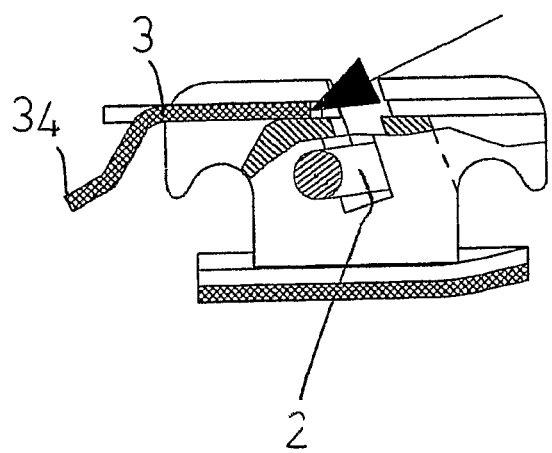
FIG. 9C is a side view, with partially sectioned parts, relating to yet another position of the mobile element as the mobile element moves from the open to the closed slot position as in FIG. 8C.

According to the example shown in FIG. 3, the element (3) has a planar portion, which is delimited by the edges or sides (30), (32), (320) and (321), and the said flexible arm (33) is bent downwardly, so that the appendix (34) of the arm (33) results lower in relation to the planar portion.

The said planar portion of the element (3) provides the very opening/closing of the slot (10) when it slides above the labial side (L) of the bracket body (1).

The orthodontic bracket disclosed above works as follows.

When the slot (10) is open, as shown in FIGS. 4, 6A, 7A and 10B, i.e. when the element (3) is moved backwards, the sides (32) of the element (3) are inside the grooves (12S) of the occlusal tie wings (12), the said surfaces (35) are in contact with the appendixes (13) of the body (1), and the appendix (34) of the arm (33) is spaced from the occlusal tie wings (12).

Figure 10A:
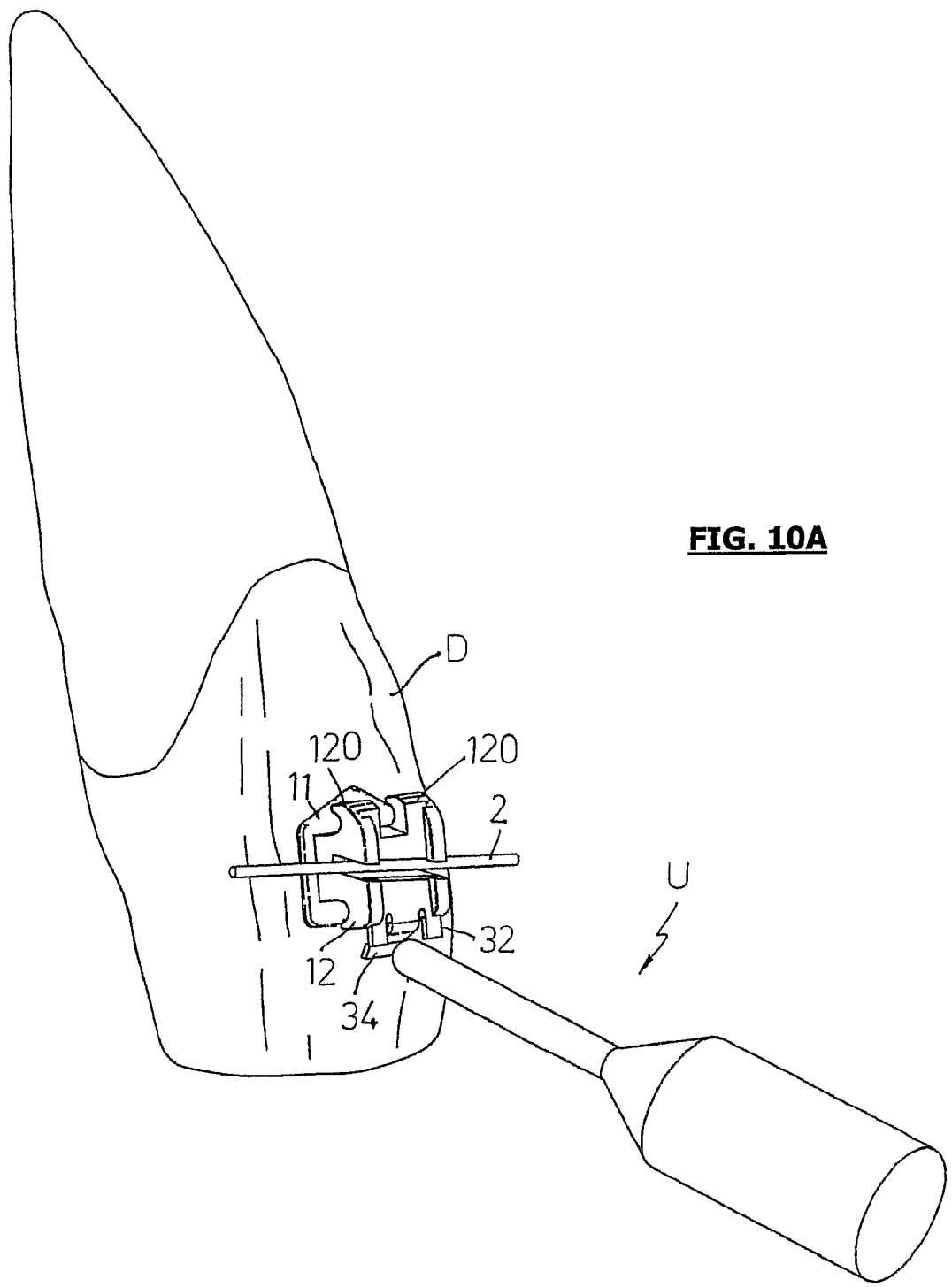
FIG. 10A is a schematic view showing the present orthodontic bracket applied to a tooth and the use of a tool while the mobile element is moved from the open to the closed slot position.
Figure 10B:
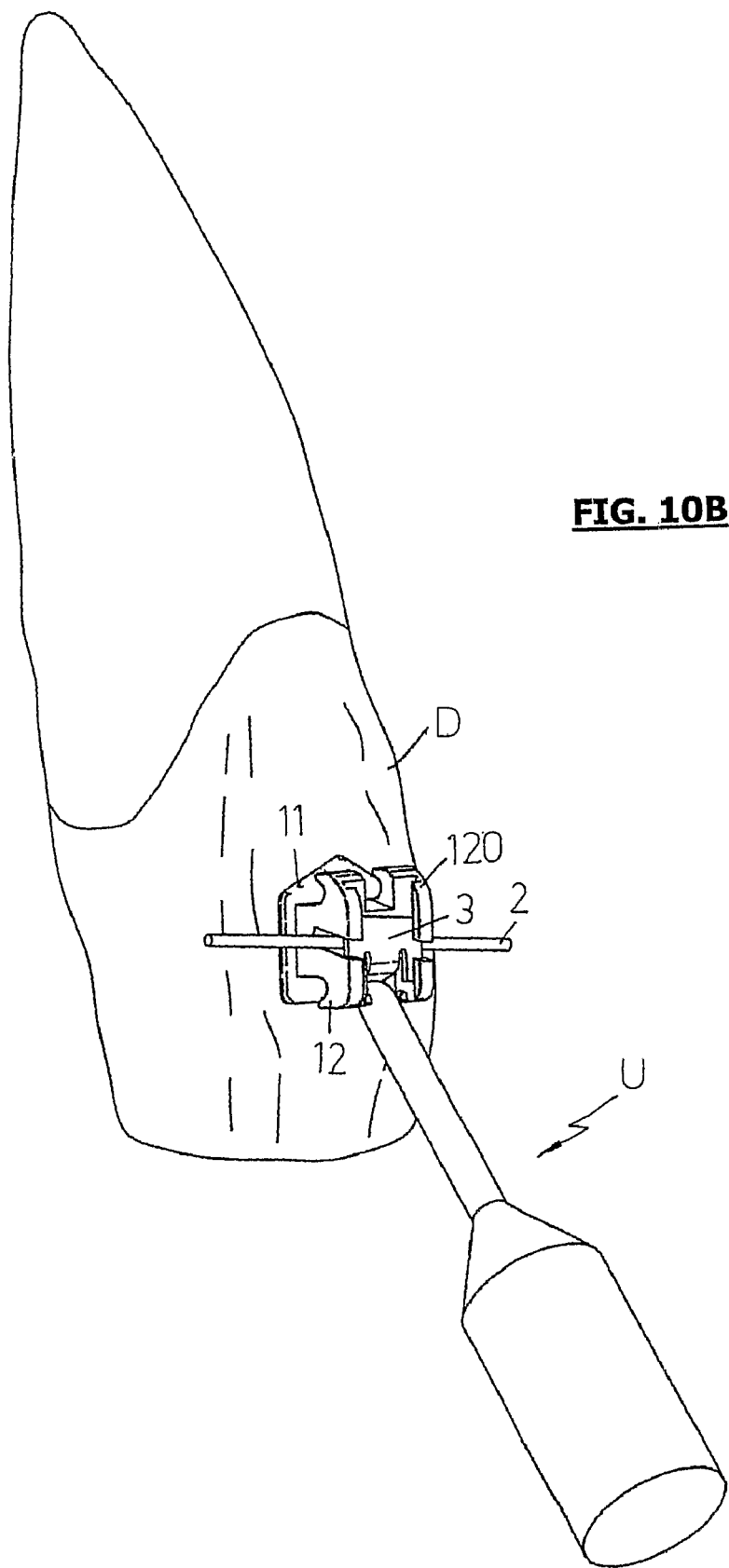
FIG. 10B is another schematic view showing the present orthodontic bracket applied to a tooth and the use of a tool while the mobile element is moved from the open to the closed slot position.

In order to close or cover the slot (10), the arm (33) is pushed forward and is bent downward, as shown by the arrows in FIGS. 6A-7C, for example by making use of a tool (U) having a rod-shaped portion as shown in FIGS. 10A and 10B. In this way, the element (3) slides over the labial side (L) of the body (1), while the sides (32) of the same element slide inside the guides constituted by the grooves (12S) of both the occlusal and gingival tie wings (12, 120), and the appendix (34) is positioned beneath the occlusal tie wings (12) which, as said before, have a concave portion (121) turned towards the base (11). In this position, due to the elasticity of the arm (33), the appendix (34) is pushed against the surfaces (121) of the tie wings (12), so that the element (3) is firmly locked in the slot (10) closing position.

Figure 11:
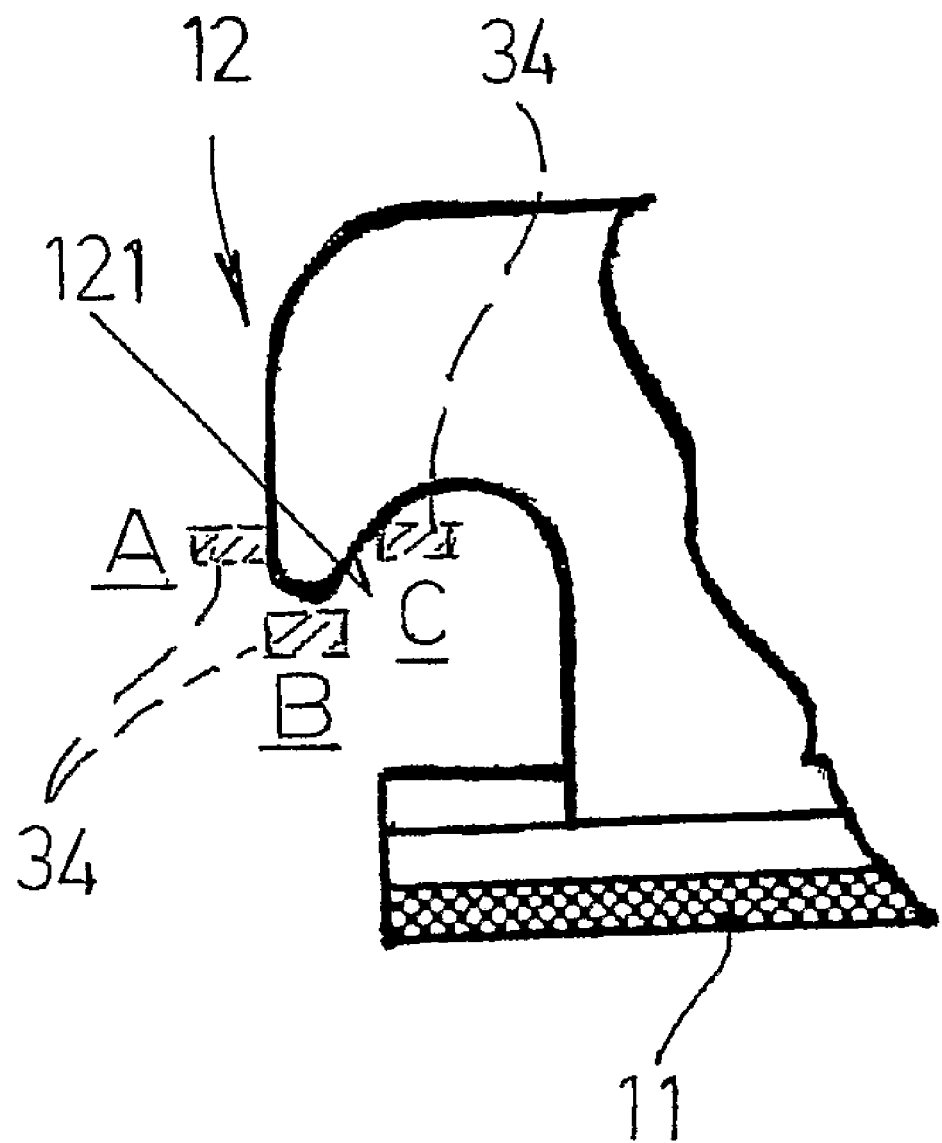
FIG. 11 is a diagram showing the positions assumed by the appendix (34) during the slot closing step.

As shown in FIG. 11, when the arm (33) is pushed forward and is bent downward, the appendix (34) comes into contact with the external surface of the tie wings (12), then it follows a curved path corresponding to the lower profile of the latter and, finally, it raises—due to the elasticity of the arm (33)—and comes into contact with the "under-wings" (121). In other words, when the arm (33) is pushed forward and is bent downward the appendix (34) assumes the position (A), then the position (B) and, finally, the position (C). Positions (A) and (C) are higher than position (B) in relation to the base (11). It is noted that the sides (32) of the element (3) move parallel to the labial side (L) of the body (1) while the appendix (34) provided by the arm (33) of the same element (3) moves along a curved path. In fact, the said sides (32) slide inside the rectilinear grooves (12S) provided on the labial side (L) of the body (1) by the occlusal tie wings (12), while the appendix (34) moves along a curved path corresponding to the lower profile of the same tie wings (12), i.e. corresponding to the profile of the lower portion (LT) of the latter.

In order to open the slot (10), by making use of the same tool (U), it is sufficient to simply push on the anterior edge (31), as shown by the arrows in FIGS. 8A-9C, thus provoking the moving of the element (3) backwards and the disengagement of the appendix (34) from its contact with the surfaces or "under-wings" (121) of the occlusal tie wings (12).

Although the above description and the accompanying drawings relate to some embodiments of the invention, the invention is not limited thereto. One skilled in the art will understand that numerous variations and modifications are possible without departing from the spirit and scope of the invention defined by the following claims.

The invention claimed is:

1. An orthodontic bracket comprising:
a body having a mesiodistal slot for receiving an archwire, a base, appendixes, a first tie wing, a second tie wing, a third tie wing and a fourth tie wing, said first tie wing, said second tie wing, said third tie wing and said fourth tie wing being mainly developed along an occlusal-gingival direction, each of said first tie wing, said second tie wing, said third tie wing and said fourth tie wing comprising a planar surface, said planar surface of said first tie wing being coplanar with said planar surface of said second tie wing, said third tie wing and said fourth tie wing, one of said appendixes extending from said planar surface of said first tie wing, another one of said appendixes extending from said planar surface of said second tie wing, said first tie wing and said second tie wing being on one side of said slot, said third tie wing and said fourth tie being on another side of said mesiodistal slot, said first tie wing, said second tie wing, said third tie wing and said fourth tie wing partially emerging over a labial side of said body, wherein said first tie wing, said second tie wing, said third tie wing and said fourth tie wing protrude externally from the body and towards the base, said first tie wing and said second tie wing comprising a curved surface having a concavity facing in a direction of the base, said first tie wing, said second tie wing, said third tie wing and said fourth tie wing defining a support means for said element to prevent the archwire from coming out of the slot;
an element, comprising a planar element portion, an elastic arm portion and concave surfaces on sides of said arm, said concave surfaces defining slots, said concave surfaces engaging said appendixes with said element in an open state, wherein said appendixes are placed on or in said slots with said element in the open state, said elastic arm portion moving along a curved path corresponding to the profile of a lower side of said tie wings while the planar element portion of said element slides along said planar surface of one or more of said first tie wing, said second tie wing, said third tie wing and said fourth tie wing above the labial side of the body, each of said first tie wing, said second tie wing, said third tie wing and said fourth tie wing comprising a rectilinear groove in which two sides of said element slide, one side of said element extending through at least a portion of said rectilinear groove of said first tie wing and at least a portion of said rectilinear groove of said third tie wing with said element in said closed position, another side of said element extending through at least a portion of said rectilinear groove of said second tie wing and at least a portion of said rectilinear groove of said fourth tie wing with said element in said closed position.

2. An orthodontic bracket according to claim 1, wherein said elastic arm portion extends transversally to the same arm.

3. An orthodontic bracket according to claim 1, wherein each of appendixes orthogonally extends from said labial side, on the inner side of one of said occlusal tie wings.

4. An orthodontic bracket according to claim 1, wherein said appendixes define a stopping means for stopping the element when the element is moved to open the slot, said one of said appendixes having a height that is less than a height of an upper first tie wing portion of said first tie wing, said another one of said appendixes having a height that is less than a height of an upper second tie wing portion of said second tie wing, the upper first and second tie wing portions being above said first and second tie wing planar surfaces.

5. An orthodontic bracket according to claim 1, wherein said element is made of a thin plate, with an anterior edge, a rear zone, and two sides intended to slide inside grooves provided by the tie wings, said two sides being adjacent to said anterior edge, said anterior edge being opposite said rear zone.

6. An orthodontic bracket according to claim 5, wherein said two sides are connected to the arm, on an end of the arm which is opposite an end with said elastic arm portion, by the same material of which the element is made, wherein longitudinal edges of said arm are spaced from inner edges of said two sides, so that said arm can flex.

7. An orthodontic bracket according to claim 6, wherein said concave surfaces have a concavity facing in a direction of said rear zone of the element.

8. An orthodontic bracket according to claim 5, wherein said two sides are connected to the arm, on an end of the arm which is opposite an end with elastic arm portion, by the same material of which the element is made, wherein longitudinal edges of said arm are spaced from inner edges of said two sides, so that said arm can flex.

9. An orthodontic bracket comprising:
a body having a mesiodistal slot, a base, a first appendix, a second appendix, a first tie wing, a second tie wing, a third tie wing and a fourth tie wing, said first tie wing, said second tie wing, said third tie wing and said fourth tie wing extending in a substantially occlusal-gingival direction, said first tie wing and said second tie wing being arranged on one side of said mesiodistal slot, said third tie wing and said fourth tie wing being arranged on another side of said mesiodistal slot;
an element comprising a planar portion and a flexible and elastic arm, said flexible and elastic arm comprising an elastic arm portion, said element being movably connected to said base such that said element moves between an open position and a closed position, each of said first tie wing and said second tie wing comprising a curved surface having a concavity facing in a direction of the base, at least a portion of each said first tie wing and said second tie wing defining a support means for supporting at least a portion of said elastic arm portion, said elastic arm portion being in contact with said curved surface of said first tie wing and said second tie wing with said element in said closed position, said element comprising a first surface on one side of said arm and a second surface on another side of said arm, said first surface defining at least a portion of a first slot, said second surface defining at least a portion of a second slot, said first surface engaging said first appendix and said second surface engaging said second appendix with said element in said open position, wherein said first appendix is arranged on or in said first slot and said second appendix is arranged on or in said second slot with said element in said open position, each of said first tie wing, said second tie wing, said third tie wing and said fourth tie wing comprising a rectilinear groove, said first appendix being adjacent to said rectilinear groove of said first tie wing, said second appendix being adjacent to said rectilinear groove of said second tie wing, one side of said element extending through at least a portion of said rectilinear groove of said first tie wing and at least a portion of said rectilinear groove of said third tie wing with said element in said closed position, another side of said element extending through at least a portion of said rectilinear groove of said second tie wing and at least a portion of said rectilinear groove of said fourth tie wing with said element in said closed position.

10. An orthodontic bracket in accordance with claim 9, wherein said elastic arm portion of the flexible arm moves along a curved path corresponding to a profile of a lower side of said first tie wings and said second tie wing and said planar portion of said element moves in a direction parallel to said labial side surface as said element moves from one of said open position and said closed position to another one of said open position and said closed position.

11. An orthodontic bracket in accordance with claim 9, wherein said elastic arm portion extends in a direction parallel to said slot.

12. An orthodontic bracket according to claim 9, wherein each of first appendix and said second appendix is perpendicular to said labial side surface, said first appendix being arranged on one side of said first tie wing, said second appendix being arranged on one side of said second tie wing.

13. An orthodontic bracket according to claim 12, wherein said first appendix and said second appendix stop movement of said element when said element is moved to said open position.

14. An orthodontic bracket according to claim 9, wherein said element is made of a thin plate, said element comprising an anterior edge, a rear zone, and two sides, said two sides being adjacent said anterior edge, said anterior edge being opposite said rear zone.

15. An orthodontic bracket according to claim 14, wherein said two sides are connected to said arm, wherein longitudinal edges of said arm are spaced from inner edges of said two sides.

16. An orthodontic bracket according to claim 15, wherein said first surface and said second surface have a concavity facing in a direction of said rear zone of the element.

17. An orthodontic bracket according to claim 9, wherein said first tie wing has a first tie wing planar surface, said second tie wing having a second tie wing planar surface, said third tie wing having a third tie wing planar surface, said fourth tie wing having a fourth tie wing planar surface, said first tie wing planar surface being coplanar with said second tie wing planar surface, said third tie wing planar surface and said fourth tie wing planar surface, at least a portion of said first wing being located above said first tie wing planar surface, at least a portion of said second tie wing being located above said second tie wing planar surface, at least a portion of said third tie wing being located above said third tie wing planar surface, at least a portion of said fourth tie wing being located at a position above said fourth tie wing planar surface, said planar portion being parallel to said first tie wing planar surface, said second tie wing planar surface, said third tie wing planar surface and said fourth tie wing planar surface, said first appendix extending from said first tie wing planar surface, said second appendix extending from said second tie wing planar surface.

18. An orthodontic bracket comprising:
a body having a mesiodistal slot extending in a mesiodistal direction, a base, rectilinear grooves, a first tie wing comprising a first tie wing planar surface, a second tie wing comprising a second tie wing planar surface, a third tie wing comprising a third tie wing planar surface and a fourth tie wing comprising a fourth tie wing planar surface, said first tie wing, said second tie wing, said third tie wing and said fourth tie wing extending in a substantially occlusal-gingival direction, said first tie wing and said second tie wing being arranged on one side of said mesiodistal slot, said third tie wing and said fourth tie wing being arranged on another side of said mesiodistal slot, said rectilinear grooves extending in said substantially occlusal-gingival direction;
an element comprising a planar portion and a flexible and elastic arm, said flexible and elastic arm comprising an elastic arm portion, said planar portion being parallel to said first tie wing planar surface, said second tie wing planar surface, said third tie wing planar surface and said fourth tie wing planar surface, each of said first tie wing, said second tie wing, said third tie wing and said fourth tie wing comprising a curved surface having a concavity facing in a direction of the base, at least a portion of each said first tie wing said element is movably connected to said base such that said element moves between an open position and a closed position, said body comprising a first appendix extending from said first tie wing planar surface and a second appendix extending from said second tie wing planar surface, said element comprising a first surface on one side of said arm and a second surface on another side of said arm, said first surface defining at least a portion of a first slot, said second surface defining at least a portion of a second slot, said first surface engaging said first appendix and said second surface engaging said second appendix with said element in said open position, wherein said first appendix is arranged on or in said first slot and said second appendix is arranged on or in said second slot with said element in said open position, one portion of said planar portion being in contact with said first tie wing planar surface and another portion of said planar portion being in contact with said second tie wing planar surface with said element in said open position, said planar portion being in contact with said first tie wing planar surface, said second tie wing planar surface, said third tie wing planar surface and said fourth tie wing planar surface with said element in said closed position.

19. An orthodontic bracket in accordance with claim 18, wherein said first tie wing comprises a first tie wing portion, said second tie wing comprising a second tie wing portion, said third tie wing comprising a third tie wing portion, said fourth tie wing comprising a fourth tie wing portion, said first tie wing portion being located a position above said first tie wing planar surface, said second tie wing portion being located at a position above said second tie wing planar surface, said third tie wing portion being located at a position above said third tie wing planar portion and said fourth tie wing portion being located at a position above said fourth tie wing planar portion, at least a portion of said first tie wing portion defining at least a portion of a first one of said rectilinear grooves, at least a portion of said second tie wing portion defining at least a portion of a second one of said rectilinear grooves, at least a portion of said third tie wing portion defining at least a portion of a third one of said rectilinear grooves, at least a portion of said fourth tie wing portion defining at least a portion of a fourth one of said rectilinear grooves, said first one of said rectilinear grooves being substantially aligned with said third one of said rectilinear grooves, said second one of said rectilinear grooves being substantially with said fourth one of said rectilinear grooves, one side of said element extending through at least a portion of said first one of said rectilinear grooves and at least a portion of said third one of said rectilinear grooves with said element in said closed position, another side of said element extending through at least a portion of said second one of said rectilinear grooves and at least a portion of said fourth one of said rectilinear grooves with said element in said closed position.

* * * * *